US009717915B2

(12) United States Patent
Maskara et al.

(10) Patent No.: US 9,717,915 B2
(45) Date of Patent: Aug. 1, 2017

(54) SYSTEM AND METHOD FOR CHANGING DEVICE PARAMETERS TO CONTROL CARDIAC HEMODYNAMICS IN A PATIENT

(71) Applicant: Cardiac Pacemakers, Inc., St. Paul, MN (US)

(72) Inventors: Barun Maskara, Blaine, MN (US); Qi An, Blaine, MN (US); Pramodsingh Thakur, White Bear Lake, MN (US); Julie Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 45 days.

(21) Appl. No.: 14/205,039

(22) Filed: Mar. 11, 2014

(65) Prior Publication Data

US 2014/0277240 A1    Sep. 18, 2014

Related U.S. Application Data

(60) Provisional application No. 61/780,484, filed on Mar. 13, 2013.

(51) Int. Cl.
*A61N 1/365* (2006.01)
*A61N 1/368* (2006.01)

(52) U.S. Cl.
CPC ........ *A61N 1/36585* (2013.01); *A61N 1/3684* (2013.01); *A61N 1/36571* (2013.01); *A61N 1/3682* (2013.01); *A61N 1/36535* (2013.01); *A61N 1/36542* (2013.01); *A61N 1/36564* (2013.01)

(58) Field of Classification Search
CPC ............ A61N 1/36571; A61N 1/36585; A61N 1/3682; A61N 1/36542; A61N 1/36564; A61N 1/36535
See application file for complete search history.

(56) References Cited

U.S. PATENT DOCUMENTS

| 5,199,428 A | 4/1993 | Obel et al. |
|---|---|---|
| 5,554,177 A | 9/1996 | Kieval et al. |
| 5,836,987 A | 11/1998 | Baumann et al. |
| 5,935,081 A | 8/1999 | Kadhiresan |

(Continued)

FOREIGN PATENT DOCUMENTS

WO    2012084044 A1    6/2012

OTHER PUBLICATIONS

Amit, G., "Heart Sound Analysis: Theory, Techniques and Applications", Advanced Research Seminar, May 2004 (41 pgs.).

(Continued)

*Primary Examiner* — Alyssa M Alter
(74) *Attorney, Agent, or Firm* — Schwegman Lundberg & Woessner, P.A.

(57) ABSTRACT

Pacing parameters may be adjusted to increase the cardiac output of a patient's heart while a patient is awake and/or active and the demand placed on the heart may be greatest, and to decrease or hemodynamic efficiency while a patient is at rest so that the heart itself has time to rest before the next period of higher demand for efficiency begins. This may aid in lessening the strain placed on the heart by making the heart work hard when needed such as when the patient is active, and by permitting the heart to "rest" when the patient is relatively inactive.

16 Claims, 7 Drawing Sheets

(56) References Cited

U.S. PATENT DOCUMENTS

| | | |
|---|---|---|
| 6,351,673 B1 | 2/2002 | Ding et al. |
| 6,409,675 B1 | 6/2002 | Turcott |
| 6,567,700 B1 | 5/2003 | Turcott et al. |
| 6,751,503 B1 | 6/2004 | Kroll |
| 7,107,093 B2 | 9/2006 | Burnes |
| 7,139,609 B1 | 11/2006 | Min et al. |
| 7,187,972 B1 | 3/2007 | Fain et al. |
| 7,336,999 B1 | 2/2008 | Koh |
| 7,558,627 B1 | 7/2009 | Turcott |
| 7,953,484 B2 | 5/2011 | Brockway et al. |
| 7,957,802 B2 | 6/2011 | Patangay et al. |
| 8,332,034 B2 | 12/2012 | Patangay et al. |
| 8,352,032 B2 | 1/2013 | Patangay et al. |
| 2004/0199210 A1* | 10/2004 | Shelchuk ........... A61N 1/36114 607/17 |
| 2006/0253301 A1 | 11/2006 | Simms et al. |
| 2009/0054945 A1* | 2/2009 | Patangay ........... A61N 1/36564 607/23 |
| 2010/0087888 A1 | 4/2010 | Maskara |
| 2010/0280500 A1 | 11/2010 | Skelton et al. |
| 2010/0318155 A1 | 12/2010 | Mahajan et al. |
| 2010/0324438 A1 | 12/2010 | Ni et al. |
| 2012/0221069 A1 | 8/2012 | Rosenberg et al. |
| 2012/0226328 A1 | 9/2012 | Dong et al. |
| 2012/0253207 A1 | 10/2012 | Sarkar et al. |
| 2012/0296228 A1* | 11/2012 | Zhang ................. A61B 5/0006 600/513 |
| 2013/0030484 A1 | 1/2013 | Zhang et al. |

OTHER PUBLICATIONS

Tavazzi, L., "Implantable monitoring devices", GVM Care and Research, Cotignola, Italy, Aug. 31, 2009 (47 pgs.).

Pei-Chin Hsieh, B.P., et al., "The amplitude ratio of the first to second heart sound is reduced in left ventricular systolic dysfunction", International Journal of Cardiology, 12161 (2009) p. 1-3.

Amit, G., et al., "Respiratory modulation of heart sound morphology", AJP—Heart, Mar. 2009, vol. 296, No. 3, H796-H805.

* cited by examiner

SYSTEM AND METHOD FOR CHANGING DEVICE PARAMETERS TO CONTROL CARDIAC HEMODYNAMICS IN A PATIENT

CROSS-REFERENCE TO RELATED APPLICATIONS

This application claims priority under 35 U.S.C. §119 to U.S. Provisional Application Ser. No. 61/780,484, filed Mar. 13, 2013, the entirety of which is incorporated herein by reference.

TECHNICAL FIELD

The present disclosure relates generally to implantable medical devices. More particularly, the present disclosure relates to systems, devices, and methods for controlling cardiac hemodynamics of a heart.

BACKGROUND

Cardiac rhythm management devices have been developed to provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Typically, leads extend into the patient's heart chamber and/or into veins of the heart. The leads often include electrodes that sense the heart's electrical signals and deliver electrical stimulation to the heart in accordance with various therapies aimed at improving cardiac function.

Pacing therapy has been used in the treatment of heart failure (HF). Heart failure causes diminished pumping power of the heart, resulting in the inability to deliver sufficient blood to meet the demands of peripheral tissues. Heart failure can cause weakness, loss of breath, and build up of fluids in the lungs and other areas. In some cases, HF can occur when deterioration of the muscles of the heart result in an enlargement of the heart and/or reduced contractility. The reduced contractility tends to decrease the cardiac output of the heart. In some cases, HF can occur when contractions of the left and right heart chambers are not synchronized properly, denoting atrial or ventricular dyssynchrony. Particularly when the left or right ventricles are affected, the unsynchronized contractions can significantly decrease the pumping efficiency and cardiac output of the heart.

BRIEF SUMMARY

The present disclosure generally relates to systems, devices, and methods for controlling cardiac hemodynamics of a heart. In one instance, a method for pacing a heart includes: pacing the heart to increase the left ventricular contractility to produce an increased cardiac output during a first period of time, and pacing the heart to decrease the left ventricular contractility relative to the left ventricular contractility achieved during the first period of time to produce a reduction in cardiac output during a second period of time. Another example method may include: pacing the heart to increase the cardiac work of the heart during a first period of time, and pacing the heart to decrease the cardiac work of the heart relative to the cardiac work achieved during the first period of time during a second period of time. Yet another example method may include: estimating a current cardiac load on the heart via an implantable pacing device; identifying a set of pacing parameters that correspond to the estimated current cardiac load on the heart using the implantable pacing device; and pacing the heart using the identified set of pacing parameters using the implantable pacing device. These are just a few example methods.

During the second period of time, it is contemplated that the heart may not be paced with pacing parameters that attempt to maximize the cardiac output of the heart. During these time periods, the heart muscle may be under less stress, and the heart muscle may be allowed to rest, recover and/or heal. In some cases, the first period of time may occur during a time when the patient is more likely to need a higher level of cardiac output, such as when the patient is awake (e.g. during the day), and the second period of time may occur when the patient is not as likely to need a high level of cardiac output, such as when the patient is asleep. In some instances, the first period of time may correspond to a period of time in which the patient has a first posture (e.g. standing), and the second period of time may correspond to when the patient has a second posture (e.g. sitting or lying down). In some instances, the first period of time may correspond to a period of time in which the patient has a first activity level, and the second period of time may correspond to when the patient has a second activity level.

Various pacing parameters may be changed to increase or decrease the ventricular contractility, cardiac output and/or cardiac work of the heart during the first and second time periods. Exemplary pacing parameters include, but are not limited to, atrial-ventricular delay (A-V delay), interventricular delay (V-V delay), pacing pulse amplitude and pacing pulse width. Alternatively, or in addition, the pacing vectors may be changed to help increase or decrease the ventricular contractility, cardiac output and/or cardiac work of a patient's heart during the first and second time periods.

The above summary of some embodiments is not intended to describe each disclosed embodiment or every implementation of the present disclosure. The Figures, and Description, which follow, more particularly exemplify certain illustrative embodiments.

BRIEF DESCRIPTION OF THE DRAWINGS

The disclosure may be more completely understood in consideration of the following description of various illustrative embodiments in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the disclosure.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Heart failure, long term pacing, ischemia, myocardial infarction and/or other factors can produce non-uniformities in the electrical, mechanical, or electromechanical properties of the myocardium. These non-uniformities can cause heart chambers to, for example, contract in an uncoordinated manner resulting in inefficient pumping action. Various electrical stimulation therapies such as, for example, cardiac resynchronization therapy (CRT) can help improve the efficiency of atrial and ventricular contractions necessary to circulate blood throughout the body. CRT results in a more coordinated contraction of the ventricles with improved pumping efficiency and increased cardiac output. Resynchronization can be achieved in certain patients by pacing at a single site, such as the left ventricle (LV). For example, a LV pace may be delivered after an appropriate delay initiated relative to aright ventricular (RV) sense or may be delivered after an appropriate delay initiated relative to an atrial sense or pace. In some configurations, resynchronization pacing may involve biventricular pacing.

A number of variables may be used, either individually or in some combination, to characterize the hemodynamic efficiency of a patient's heart. These variables may include, but are not limited to, systolic blood pressure, diastolic blood pressure, mean arterial pressure, pulse pressure, heart rate, left ventricular maximum dP/dT (LV dP/DT Max), LV contractility, cardiac output, cardiac index, stroke volume, stroke volume index, stroke volume (SV) compliance, SV resistance, brachial artery compliance, brachial artery distensibility, brachial artery resistance, as well as others. In some instances, maximum LV dP/dT and/or LV contractility may be used to characterize the hemodynamic efficiency of the heart. It should be noted that the hemodynamic efficiency of a patient's heart is different from the energy efficiency of a patient's heart which is related to cardiac work.

Different pacing parameters may be adjusted and/or optimized to increase and/or decrease the hemodynamic efficiency of the heart. Exemplary pacing parameters that may be adjusted and/or changed to increase and/or decrease the hemodynamic efficiency of the heart include, but are not limited to, atrial-ventricular delay (A-V delay), interventricular delay (V-V delay), interatrial delay (A-A delay), intersite pacing delays, tracking or non-tracking operation, pacing sites, pacing vectors, pacing rate limits, pacing pulse amplitude, pacing pulse width, as well as others.

In some cases, one or more pacing parameters may be controlled so that the hemodynamic efficiency of a patient's heart may be varied with changes in a patient's activity level, posture, and/or circadian rhythm of the patient. In some cases, different pacing parameters may be selected based on a detected change or changes to a patient's activity level, posture, and/or circadian rhythm. For example, in some cases, a first set of pacing parameters may be selected to increase contractility of the heart during a first period of time, and a second set of pacing parameters may be selected to intentionally decrease contractility of the heart during a second period of a time relative to the contractility of the heart achieved during the first time period. The first and second periods of time may correlate to period of times in which a patient experiences a change in activity level, a change in posture, and/or a change in their circadian rhythm. For example, in some cases, the first period of time may correspond to a period of time in which the patient may be more "active" such as when the patient is engaging in some level of physical activity and/or is awake. Similarly, the second period of time may correspond to a period of time in which the patient may be less active and/or relatively inactive, such as when the patient is sitting, reading, knitting, watching television, resting, and/or sleeping. It should be noted that, in many cases, while the contractility of the heart may be decreased during the second time period relative to the contractility of the heart during the first time period, the contractility of the hear that is achieved during the second time period still may be at or, in some cases, greater than, the intrinsic baseline contractility of the patient's heart. However, in some cases, when appropriate, the contractility of the heart achieved during the second period may be below the intrinsic baseline contractility of the patient's heart. Increasing and/or maximizing contractility of the heart during a first period in which the patient may be more active may help provide adequate heart function to support the activity. Intentionally decreasing the contractility of the heart during a second period in which the patient is less active, may provide the heart with time to rest, recover and/or heal.

Figure 1:
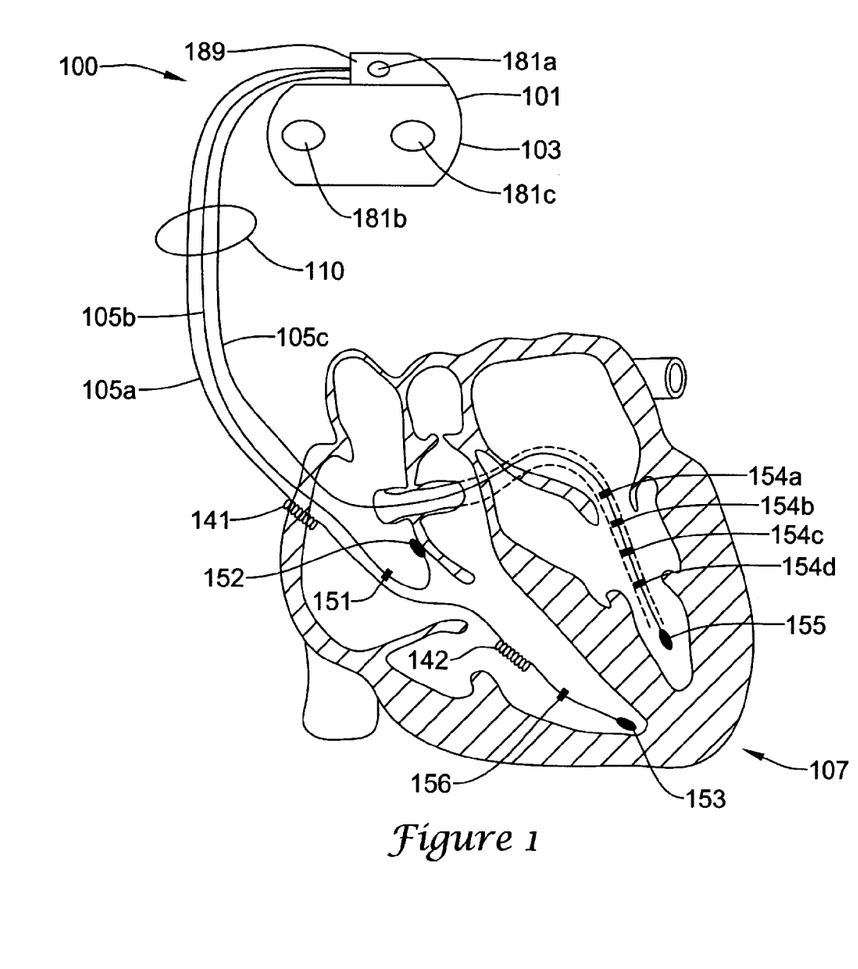
FIG. 1 is a schematic view of a system including an implantable medical device (IMD) coupled to one or more leads disposed within a patient's heart.

FIG. 1 is a schematic view of an illustrative system 100 that may be used to deliver a therapy to a patient's heart in accordance with the various embodiments of the present disclosure as described herein. As shown in FIG. 1, the system 100 may include an implantable medical device (IMD) 101 coupled to a lead system 110 having one or more electrical leads 105a-105c for delivering an electrical stimulus therapy to a patient's heart 107. Exemplary IMDs 101 suitable for use with the system 100 include, but are not limited to, a pacemaker, a defibrillator, a cardiac resynchronization therapy (CRT) device, or a combination of such devices. Additionally, the system 100 may include communications circuitry disposed within the housing 103 of the IMD 101 for facilitating communication between the CRM circuitry and a patient-external device, such as an external programmer or advanced patient management (APIA) system. The communications circuitry may also facilitate unidirectional or bidirectional communication with one or more implanted, external, cutaneous, or subcutaneous physiologic or non-physiologic sensors, patient-input devices and/or information systems.

As shown in the example of FIG. 1, portions of the lead system 110, including leads 105a-c, may be disposed within the patient's heart 107. The illustrative leads system 110 includes cardiac pace/sense electrodes 151-156 positioned in, on, or about one or more heart chambers for sensing electrical signals from the patient's heart 107 and/or delivering pacing pulses to the heart 107. The intracardiac sense/pace electrodes 151-156, such as those shown in FIG. 1, may be used to sense and/or pace one or more chambers of the heart, including the left ventricle, the right ventricle, the left atrium and/or the right atrium. In some cases, as shown in FIG. 1, the lead system 110 may include one or more defibrillation electrodes 141, 142 for delivering defibrillation/cardioversion shocks to the heart. In the illustrative example provided by FIG. 1, the left ventricular lead 105c can incorporate multiple electrodes 154a-154d positioned at various locations within, on or about the left ventricle. Stimulating the left ventricle at multiple locations or at a single selected location may provide for increased cardiac output in a patients suffering from heart failure. In accordance with various embodiments described herein, one or more of the electrodes 154a-154d can be selected for pacing the left ventricle. In other embodiments, leads having multiple pacing electrodes positioned at multiple locations within a chamber, such as the one illustrated by the left ventricular lead 105c of FIG. 1, may be implanted within any or all of the head chambers. Electrical stimulation pulses may be delivered to the chambers via the selected electrodes according to a timing sequence and output configuration that enhances cardiac function. In some cases, the IMD may use different combinations of electrodes for pacing and/or sensing, depending on the circumstances. Each combination of pacing electrodes used can be considered a "vector".

Portions of the housing 103 of the implantable medical device (IMD) 101 may optionally serve as one or multiple can or indifferent electrodes. The housing 103 is illustrated as incorporating a header 189 that may be configured to facilitate removable attachment between one or more leads 110 and the housing 103. The housing 103 and/or header 189 may include any number of electrodes positioned anywhere in or on the housing 103 and/or header 189. In some cases, as shown, the housing 103 of the IMD 101 may include one or more can electrodes 181b, 181c. The header 189 of the MD 101 may also include one or more indifferent electrodes 181a.

The cardiac electrodes and/or other sensors disposed within or on the housing 103 or lead system 110 of the system 100 may produce signals used for detection and/or measurement of various physiological parameters, such as, but not limited to: transthoracic impedance, respiration rate, minute ventilation, heart rate, cardiac dyssynchrony, activity, posture, circadian rhythm, blood chemistry, oxygen saturation, heart sounds, wall stress, wall strain, hypertrophy, inter-electrode impedance, electrical delays (e.g. A-V delay, A-A delay, A-V delay, V-V delay, etc.), cardiac chamber pressure such as, for example, left ventricular pressure, cardiac output, temperature, heart rate variability, depolarization amplitudes, depolarization timing, cardiac energy consumption, cardiac work and/or other physiological parameters. Such parameters can be monitored to determine whether a particular set of pacing parameters improves hemodynamic efficiency of the heart and/or cardiac output relative to other pacing parameters under certain conditions. In addition, monitoring of such parameters may aid in the selection of pacing parameters to increase the hemodynamic efficiency and/or cardiac output of the heart and/or decrease the hemodynamic efficiency and/or cardiac output of the heart as needed or desired depending upon a patient activity level, posture, and/or circadian rhythm.

In some configurations, the system 100 may incorporate one or more transthoracic impedance sensors that may be used to acquire a patient's respiratory waveform, and/or to acquire other information. Information from the transthoracic impedance sensor may be used to, for example, adapt the rate of pacing to correspond to the patient's activity or metabolic needs.

The system 100 may also include one or more physiological process sensors such as, for example, a temperature sensor, a blood pressure sensor, a respiratory rate/respiratory rate a respiratory rate/respiratory rate variability sensor 262, a tidal volume/MV sensor, an activity sensor, a heart rate/heart rate variability sensor, a posture sensor, or an accelerometer or microphone.

Additionally, the system 100 may incorporate one or more sensors to monitor heart sounds. The term "heart sound" refers to any heart sound (e.g., S1) and any components thereof (e.g., M1 component of S1, indicative of mitral valve closure). The term heart sound also includes audible and inaudible mechanical vibrations caused by cardiac activity that can be sensed with an accelerometer or the like. Heart sounds include the "first heart sound" or S1, the "second heart sound" or S2, the "third heart sound" or S3, the "fourth heart sound" or S4, and their various sub-components. S1 is indicative of, among other things, mitral valve closure, tricuspid valve closure, and aortic valve opening. S2 is indicative of, among other things, aortic valve closure and pulmonary valve closure. S3 is a ventricular diastolic filling sound often indicative of certain pathological conditions including heart failure. S4 is a ventricular diastolic filling sound resulted from atrial contraction and is usually indicative of pathological conditions. Exemplary sensors that may be used to detect heart sounds include, but are not limited to: accelerometers, microphones, acoustical sensors, strain gauges and piezoelectric sensors.

Monitoring heart sounds can be used to help provide a measure of hemodynamic performance parameters. For example, heart sounds signals obtained from heart sound sensors may be indicative of timing, strength, and frequency characteristics related to the heart sounds. Measuring these characteristics may help determine the condition and/or state of a patient's hemodynamic system, and may facilitate selection of pacing parameters that may be used to either increase or decrease the patient's hemodynamic efficiency and/or cardiac output under certain conditions.

Figure 2:
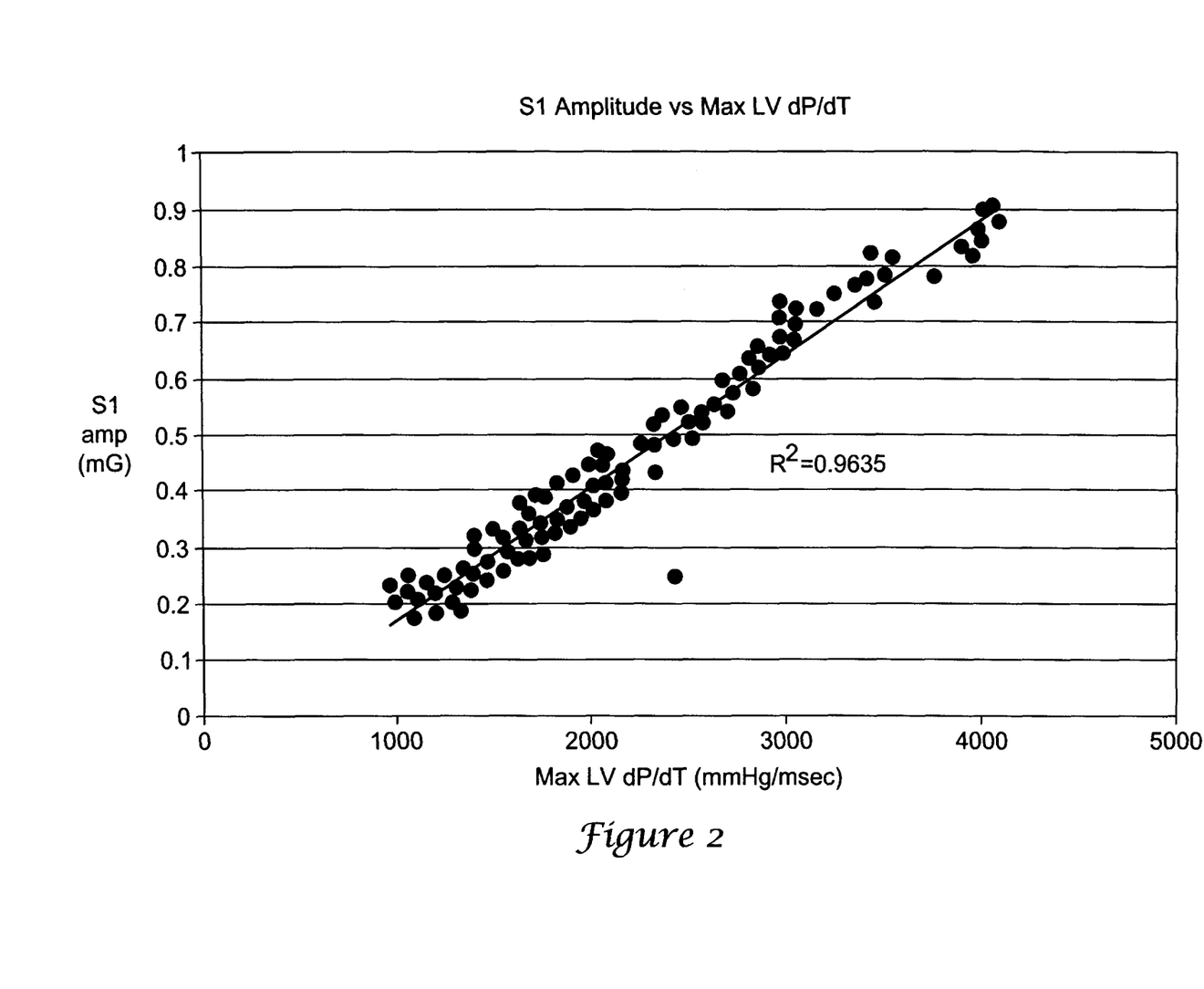
FIG. 2 is a graph showing a strong correlation between the amplitude of the first heart sound S1 and the maximum left ventricle (LV) change-in-pressure versus change in time (dP/dT) of a heart.

In one example, and as shown in FIG. 2, there is a strong correlation between the amplitude of the first heart sound S1 and the maximum left ventricle (LV) change-in-pressure versus change in time (dP/dT) of a heart. Maximum LV dP/dT can be used to assess LV contractility of the heart, and thus may provide a measure of cardiac output of the heart 107. Measuring S1 with a heart sound sensor, and correlating it to a maximum LV dP/dT of a patient's heart, may facilitate selection of pacing parameters that increase and/or decrease the maximum LV dP/dT of a patient's heart under certain conditions. For example a first set of pacing parameters may be selected to increase the maximum LV dP/dT of a patient's heart during a first period of time, such as when the patient may be more active, and a second set of pacing parameters may be selected to decrease or provide a smaller increase in the maximum LV dP/dT of a patient's heart during a second period of time relative to the LV dP/dT achieved during the first time period, such as when the patient may be less active or relatively inactive.

Figure 3:
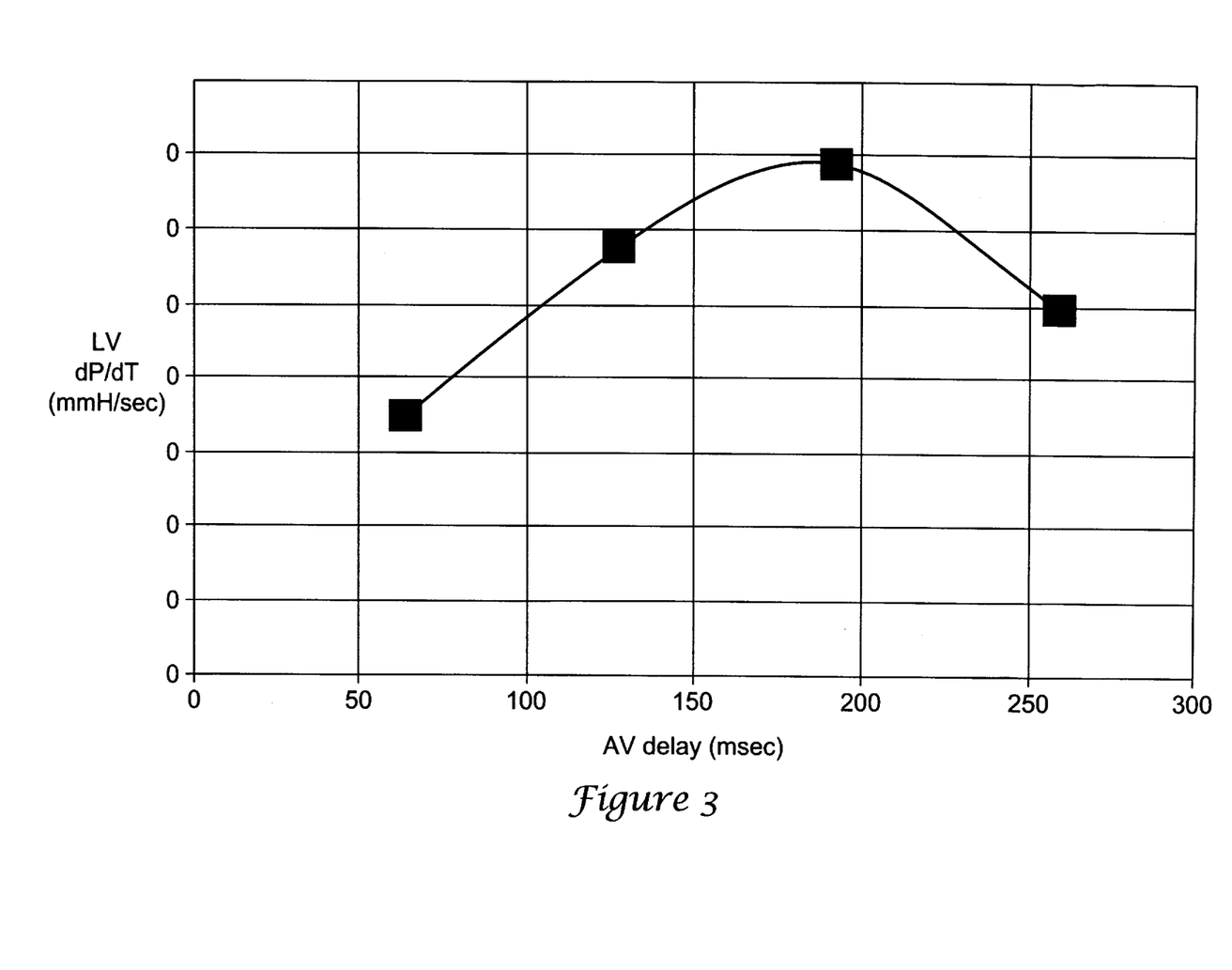
FIG. 3 is a graph showing an illustrative relationship between an AV delay pacing parameter and the resulting maximum LV dP/dT of a patient's heart.

Exemplary pacing parameters that may be adjusted and/or changed to increase and/or decrease the hemodynamic efficiency and/or cardiac output of the heart include, but are not limited to, atrial-ventricular delay (A-V delay), interventricular delay (V-V delay), interatrial delay (A-A delay), intersite pacing delays, tracking or non-tracking operation, pacing sites, pacing vectors, pacing rate limits, pacing pulse amplitude, pacing pulse width, as well as others. In one example, the A-V delay may be changed by the IMD 101 to change the maximum LV dP/dT of a patient's heart, and thus the hemodynamic efficiency and/or cardiac output of the patient's heart. Depending upon the intrinsic hemodynamic efficiency and/or cardiac output the output of the patient's heart, a shorter or longer AV delay may be selected to decrease LV contractility and thus, reduce the energy consumption of the heart. FIG. 3 is a graph showing an illustrative relationship between an AV delay pacing parameter and the resulting maximum LV dP/dT of a patient's heart. In this example, during a first period of time, the IMD 101 may select an A-V delay of about 200 msec in order to increase LV dP/dT and thus the hemodynamic efficiency and/or cardiac output of the patient's heart. Then, during a second period of time, the IMD 101 may select an A-V delay of about 100 or 250 msec to intentionally decrease the maximum LV dP/dT relative to the LV dP/dT achieved during the first time period and thus, decrease the hemodynamic efficiency and/or cardiac output of the patient's heart. Additionally, intentionally decreasing the maximum LV dP/dT relative to the LV dP/dT achieved during the first time period may also reduce the energy consumption of the heart. The second period of time may be when the patient is expected be less active, such as during sleep. Intentionally decreasing the hemodynamic efficiency and/or cardiac output of the heart during the second period of time relative to the hemodynamic efficiency and/or cardiac output achieved during the first period of time may provide the heart with time to rest, recover and/or heal.

In some cases, the IMD 101 may incorporate monitoring sensors that may monitor the hemodynamic efficiency and/or cardiac output of the patient's heart during the adjustment of one or more pacing parameters, as described herein. Such data collected by the monitoring sensors may be indicative of impedance, S3, tidal volume, respiration rate, and/or rapid shallow breathing, but are not limited to these. In one example, the IMD 101 may include monitoring sensors that may provide data that are indicative of congestion which may worsen if the hemodynamic efficiency and/or cardiac output of the heart is decreased. During adjustment of the one or more pacing parameters to decrease the hemodynamic efficiency and/or cardiac output of the heart during a second period of time relative to the hemodynamic efficiency and/or cardiac output achieved during a first period of time, if the sensor(s) indicate that the adjustment of the one or more pacing parameters may adversely impact the function of the patient's heart, then the IMD 101 may be configured to revert to the first set of pacing parameters selected to increase the hemodynamic efficiency and/or cardiac output of the patient's heart.

Figure 4:
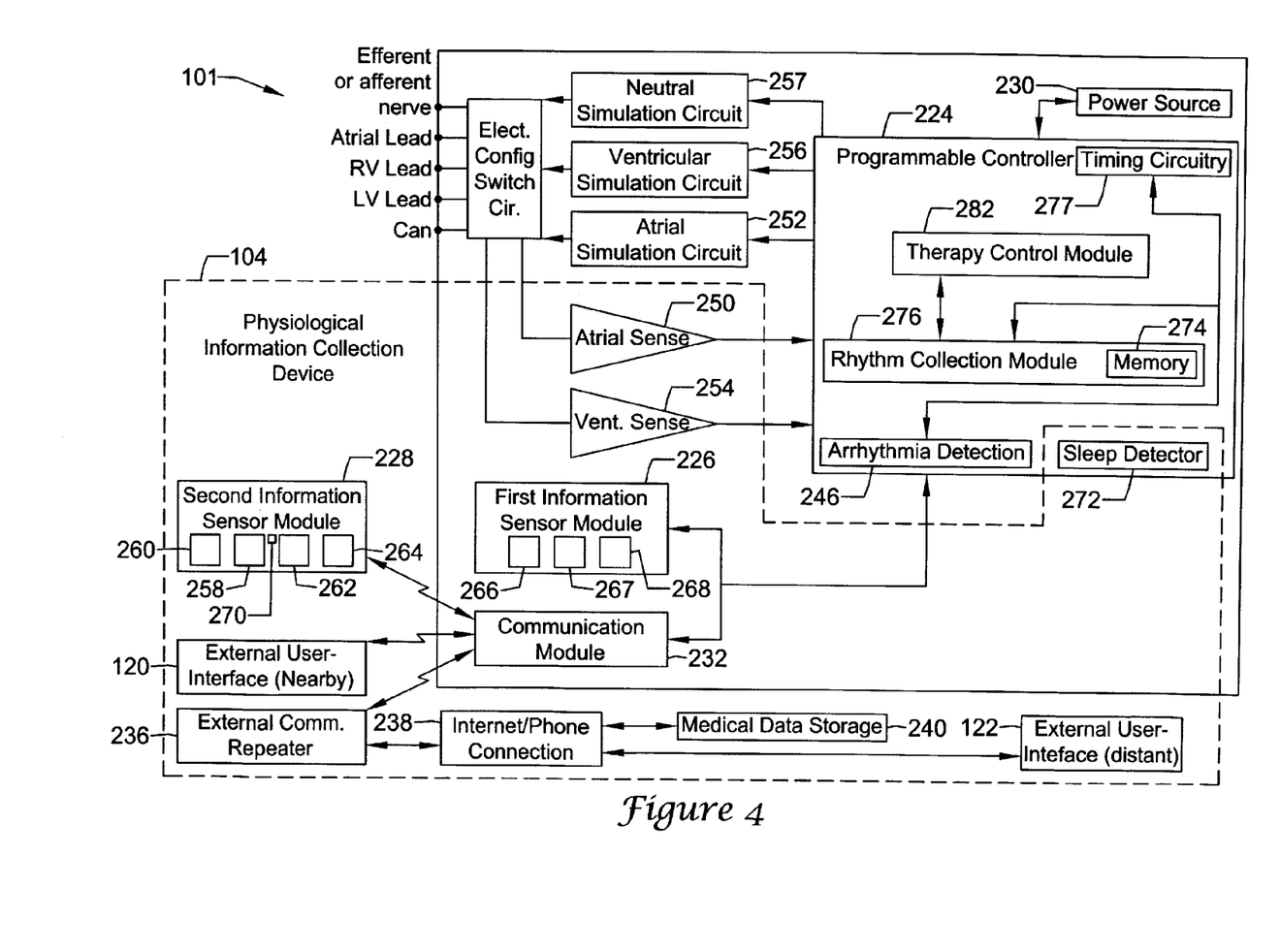
FIG. 4 is a schematic block diagram of an illustrative IMD.

FIG. 4 is schematic block diagram of an IMD 101 that may be used to adjust one or more sets of pacing parameters to help control the hemodynamic efficiency and/or cardiac output of a patient's heart under select conditions. As shown, the IMD 101 may include electronic circuitry components that are enclosed in a hermetically-sealed enclosure, such as housing 103 shown in FIG. 1. It should be noted that FIG. 4 shows just one conceptualization of various modules, circuits, and interfaces of system 100, which are implemented either in hardware or as one or more sequences of steps carried out on a microprocessor or other controller. Such modules, devices, and interfaces are illustrated separately for conceptual clarity; however, it is to be understood that the various modules, devices, and interfaces of FIG. 4 need not be separately embodied, but may be combined or otherwise implemented. The IMD 101 may be powered by a power source 230, such as a battery, which provides operating power to all the IMD internal modules and circuits shown in FIG. 4. In certain examples, the power source 230 should be capable of operating at low current drains for long periods of time and also be capable of providing high-current pulses (for capacitor charging) when the patient requires a shock pulse.

As shown in the illustrative example of FIG. 4, IMD 101 may include a physiological information collection device 104 adapted to sense or receive information about at least one physiological process having a circadian rhythm. In varying examples, the at least one physiological process includes one or more of body temperature (core or peripheral), heart rate, heart rate variability, respiration rate, respiration rate variability, minute ventilation, activity, blood pressure, posture, tidal volume, sleep duration, thoracic impedance, and heart sounds. Circadian rhythm representative signals associated with the at least one physiological process may be output to a programmable controller 224 where they may be used to determine an electrical stimulation therapy. Additionally or alternatively, a time of the circadian rhythm representative signal collection may be output to the programmable controller 224 and used to determine a set of pacing parameters for controlling a hemodynamic efficiency and/or cardiac output of a patient's heart 107 based, at least in part on their circadian state (e.g. sleep or awake).

The hemodynamic demand placed on a patient's heart decreases when the patient is less active, lying down, resting, and/or sleeping. Thus, therapy may be controlled to increase hemodynamic efficiency and/or cardiac output of a patient's heart while a patient is awake and/or active and the demand placed on the heart may be greatest, and to decrease or the hemodynamic efficiency and/or cardiac output while a patient is at rest so that the heart itself has time to rest before the next period of higher demand begins.

As shown in FIG. 4, the physiological information collection device 104 may include an atrial sensing circuit 250, a ventricular sensing circuit 254, a first information sensor module 226, a second information sensor module 228, and a communication module 232. In some instances, the physiological information collection device 104 may include a (nearby) external user interface 120 (e.g., a home station device), an external communication repeater 236, an Internet or other communication network connection 238, a computerized medical data storage 240, or a (distant) external user interface 122 (e.g., a physician station device).

The atrial 250 and ventricular 254 sensing circuits, the first information sensor module 226, and the communication module 232 may be directly coupled to the programmable controller 224; while the second information sensor module 228, the (nearby) external user interface 120, and the external communication repeater 236 may be communicatively coupled with the communication module 232 via telemetry, and thus may also be in communication with the programmable controller 224. In this example, the communication module 232 may be capable of wirelessly communicating with the computerized medical data storage 240 or the (distant) external user interface 122, such as by using the external communication repeater 236 and the Internet/phone connection 238. In one example, the nearby 120 or distant 122 external user interface may control, load and/or retrieve information from the IMD 101, and may be adapted to process and display (e.g., textually or graphically) such information obtained.

The atrial 250 and ventricular 254 sensing circuits may be selectively coupled to the atrial lead 105a, the right ventricular lead 105b, and/or or the left ventricular lead 105c, via an electrode configuration switching circuit 244, for detecting the presence of intrinsic cardiac activity in the corresponding chambers of the heart 107. These intrinsic heart activity signals typically include depolarizations that propagate through the circulatory system. The depolarizations cause heart contractions for pumping blood through the circulatory system. The atrial 250 and ventricular 254 sensing circuits may include dedicated sense amplifiers, multiplexed amplifiers, shared amplifiers, or other signal processing circuits to extract depolarizations or other useful information from the intrinsic heart activity signals. For instance, each of the atrial 250 or ventricular 254 sensing circuits may employ one or more low power, precision amplifier with programmable or automatic gain, bandpass filtering, or a threshold detection circuit, to selectively sense the cardiac signal of interest. For arrhythmia detection 246, the IMD 101 may include the atrial 250 and ventricular 254 sensing circuits to sense cardiac signals for determining whether a rhythm is normal or pathologic.

For thoracic impedance detection, the IMD 101 may inject an electrical stimulus current of known or attainable value (e.g., via the ventricular 256 or atrial 250 stimulation circuits) to one or more implanted electrodes, and measure (e.g., via the ventricular 254 or atrial 250 sense circuits) the resulting voltage using one or more other implanted electrodes. Using information about the current and the resulting voltage, the IMD 101 may calculate impedance by taking a ratio of resulting voltage to injected current. This measurement may be repeated over time to detect changes in impedance (and thus, for example, changes in fluid amount in the lungs). A reduction in thoracic impedance may indicate the presence of an increase in fluid within the lungs. Conversely, a fluid decrease in the lungs may correspond to an increase in thoracic impedance sensed.

In FIG. 4, the first 226 and second 228 information sensor modules may include one or more physiologic process sensors, such as a temperature sensor 260, a blood pressure sensor 258, a respiratory rate/respiratory rate variability sensor 262, a tidal volume/MV sensor 264, an activity sensor 270, a heart rate/heart rate variability sensor 266, a posture sensor 268, or an accelerometer or microphone 267 for sensing heart sounds. In one example, each information sensor module 226, 228 may include one or more interface circuits that receive one or more control signals and preprocesses the sensor signal(s) received. In another example, the first 226 and second 228 information sensor modules may be combined as a single module.

In some cases, the programmable controller 224 may include a sleep detection module 272, which receives signals from the various physiological information sensors 258-270 or the nearby external user interface 120 to determine whether the patient is in a state of sleep, and in some cases, the quality of such sleep. In some examples, the programmable controller 224 may determines whether the patient is attempting to fall asleep based on whether the subject is or is not in a recumbent position, determinable via, for example, the posture sensor 268.

There are a number of other ways in which the programmable controller 224 may identify when a patient is attempting to sleep. In one example, the programmable controller 224 may identify the time that the patient begins attempting to fall asleep based on an indication received from the subject, such as via nearby external user interface 120 and the communication module 232. In another example, the programmable controller 224 may identify the time the patient begins attempting to fall asleep based on the activity level of the patient determined via the activity sensor 270. The activity sensor 270 may include one or more accelerometers, gyros, bonded piezoelectric crystals that generate a signal as a function of subject activity pattern, such as body motion, foot strikes or other impact events, and/or any other suitable sensor. Additionally or alternatively, the activity sensor 270 may include one or more electrodes that generate an electromyogram ("EMG") signal as a function of muscle electrical activity, which may indicate the activity level of the patient. The electrodes may, for example, be located in the legs, abdomen, cheek, back, or buttocks of the patient to detect muscle activity associated with walking, running, or the like.

The programmable controller 224 may include various functional modules, circuits, and detectors, one conceptualization of which is illustrated in FIG. 4. Among other things, the programmable controller 224 may include control circuitry, a RAM or ROM memory 274, logic and timing circuitry 277 to keep track of the timing of sensing or receiving circadian rhythm and/or other signals associated with physiological processes of the patient, for example, and I/O circuitry. Additionally, the programmable controller 224 may include a rhythm collection module 276 that receives from the physiological information collection device 104 information about the at least one physiological process having a circadian rhythm. The rhythm collection module 276 may include the memory 274 to store signals representative of such circadian rhythm(s) and may further classify such rhythm(s) as being associated with one or more of body temperature (core or peripheral), heart rate, heart rate variability, respiration rate, respiration rate variability, minute ventilation, activity, blood pressure, posture, tidal volume, sleep quality or duration, thoracic impedance, or heart sounds.

In some embodiments, a therapy control module 282 may be programmed to select the most appropriate pacing parameters for increasing and/or decreasing the hemodynamic efficiency and/or cardiac output of a patient's heart under selected conditions. The therapy control module 282 may be programmed to select a first set of pacing parameters for increasing the hemodynamic efficiency and/or cardiac output of a patient's heart during a first period of time based, at least in part, on the information collected by the physiological sensors 258-270, the sleep detection module 272, and/or the rhythm collection module 276. Similarly, the therapy control module 282 may be programmed to select a second set of pacing parameters for decreasing the hemodynamic efficiency and/or cardiac output of a patient's heart during a second period of relative to the hemodynamic efficiency and/or cardiac output of the patient's heart during the first period of time based, at least in part, on the information collected by the physiological sensors 258-270, the sleep detection module 272, and/or the rhythm collection module 276.

Various pacing parameters may be used to increase or decrease the cardiac output of the heart under programmed conditions. Exemplary pacing parameters that may be adjusted and/or optimized to increase and decrease the hemodynamic efficiency and/or cardiac output of the heart include, but are not limited to: atrial-ventricular delay (A-V delay), interventricular delay (V-V delay, interatrial delay (A-A delay), intersite pacing delays, tracking or non-tracking operation, pacing pulse amplitude, pacing pulse width, pacing sites, pacing vectors, pacing rate limits, and/or the like. In some cases, the one or more pacing parameters may be adjusted to increase and decrease the left ventricular contractility to produce a corresponding increased and decreased cardiac output.

Figure 5:
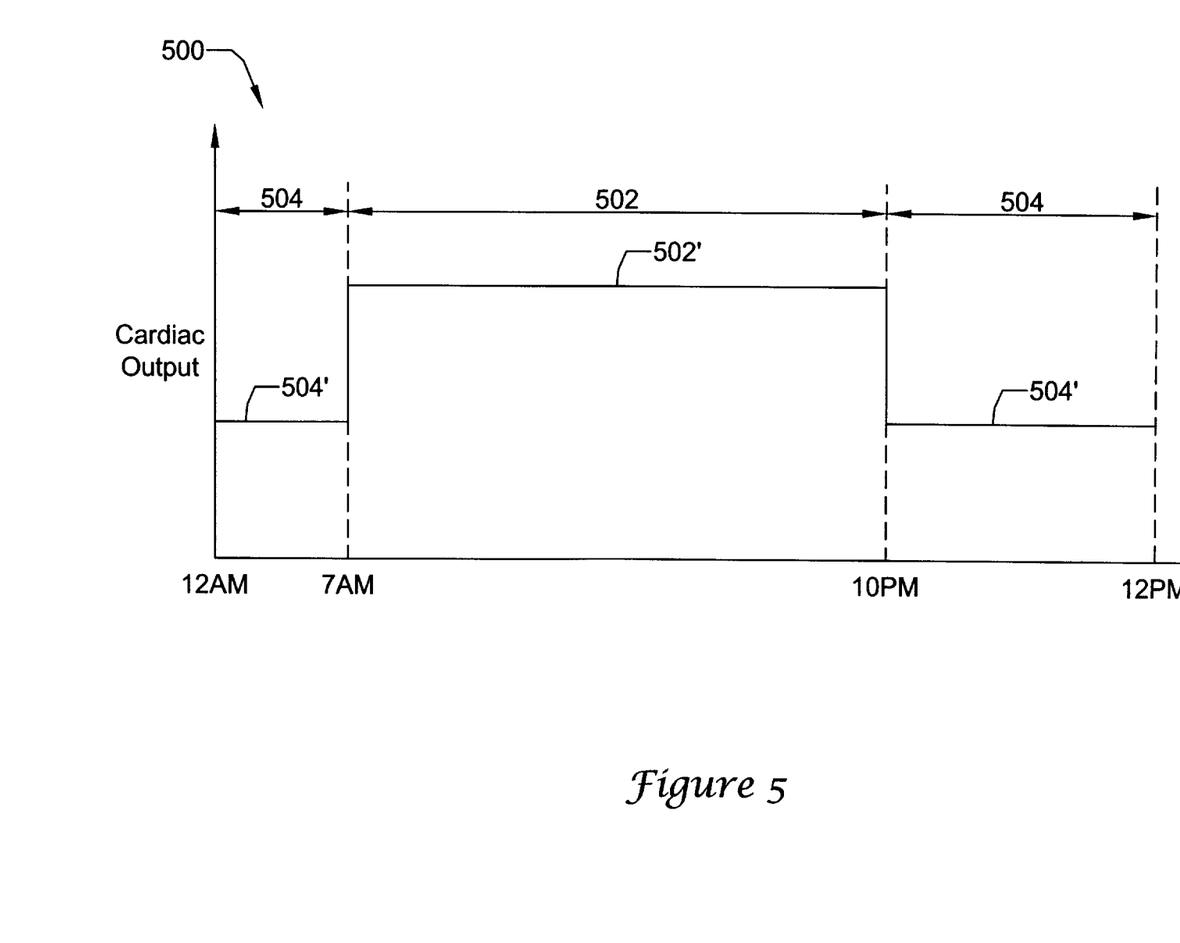
FIG. 5 is a timing diagram showing an illustrative first period of time where the heart is paced to produce in increased cardiac output and an illustrative second period of time where the heart is paced to intentionally produce a decreased cardiac output.

In some cases, the first period of time may correspond to a period of time in which the patient is more active or awake, and the second period of time may correspond to a time in which the patient is less active or asleep. For example, the first period of time may correspond to a wake period during a circadian rhythm of the patient and the second period of time may correspond generally to a sleep period during a circadian rhythm of the patient. One such example is shown in FIG. 5, which shows a timing diagram 500 of an illustrative first period of time 502 where the heart is paced to produce in increased cardiac output 502', and an illustrative second period of time 504 where the heart is paced to intentionally produce a decreased cardiac output 504'. The first period of time 504 in FIG. 5 may correspond to a time in which the patient is awake, and the second period of time 504 may correspond to a time in which the patient is asleep, sometimes in accordance with the circadian rhythm of the patient.

In another non-limiting example, the first period of time may correspond to when the patient has a first posture (e.g. standing), and the second period of time may correspond to a period of time when the patient has a second posture (e.g. sitting or lying down). In yet another example, the first period of time may correspond to a period of time when the patient is at a first activity level (e.g. engaging in some level of physical activity), and the second period of time may correspond to a period of time when the patient is at a second activity level that is different from the first activity level (e.g. resting, sitting, reading, etc.). These are just some examples.

In some cases, the therapy control module 282 of FIG. 4 may be programmed to pace the heart to increase and decrease the cardiac work of the heart, which increases and decreases the cardiac output. The cardiac work of the heart may be estimated based on the area defined by a Pressure-Volume (PV) loop. In some cases, heart sounds may be used to estimate pressure changes and impedance may be used to estimate volume changes of the heart. The therapy control module 282 may be configured to pace the heart using a first set of pacing parameters to increase the cardiac work of the heart during a first period of time, and to pace the heart using a second set of pacing parameters to decrease the cardiac work (relative to the cardiac work achieved during the first period of time), during a second period of time. In some cases the cardiac work achieved during the second period of time may be less than about 90 percent, less than about 80 percent, less than about 70 percent, less than about 60 percent or more of the cardiac work achieved during the first period of time. In some cases, the cardiac work achieved during the second period of time may range from about 50 percent to about 90 percent less than the cardiac work achieved during the first period of time.

Figure 6:
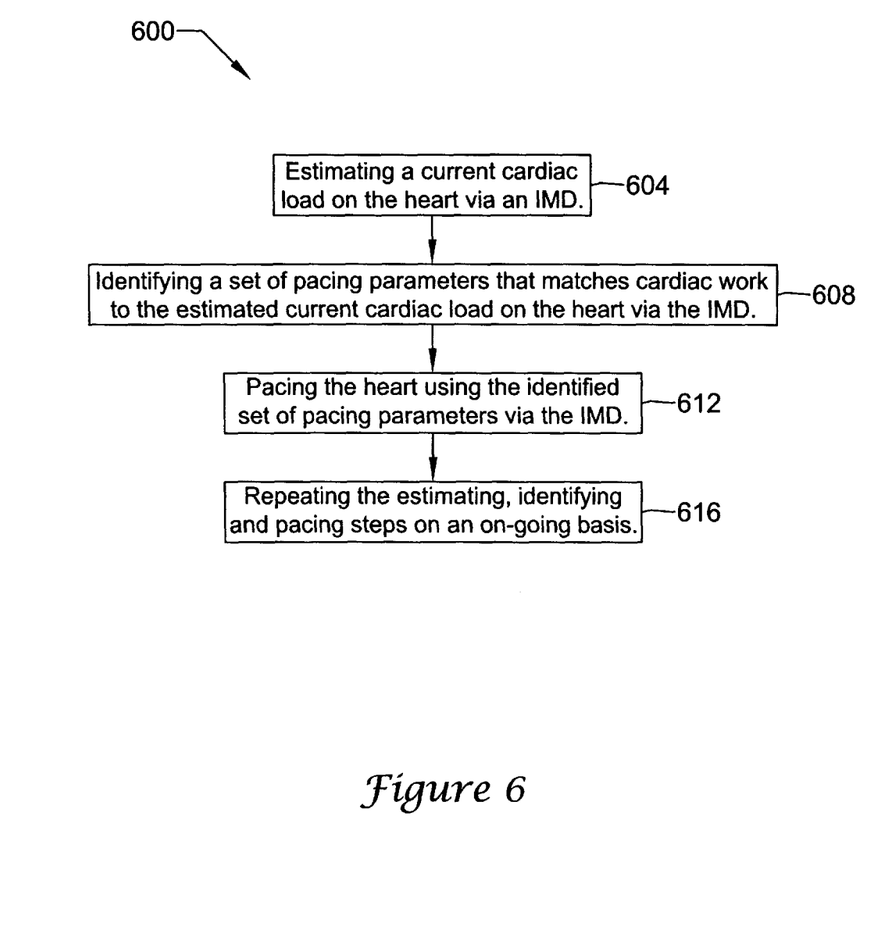
FIG. 6 is a flow chart of an illustrative method for pacing a patient's heart using an IMD.

FIG. 6 is a flow chart of an illustrative method 600 for pacing the heart using the IMD 101 to increase and/or decrease the cardiac work to match a cardiac load of a heart. According to the illustrative method, the programmable controller 224 may estimate a current cardiac load on a patient's heart (Block 604). The estimation of current cardiac load may be based on one or more parameters including, but not limited to: a time of day, a patient's posture, and/or a measure related to minute ventilation. These are just some examples. In response, the therapy control module 282 may be programmed to identify a set of pacing parameters that causes the cardiac work to match the estimated current cardiac load of the patient's heart (Block 608). In some cases, the therapy control module 282 may be configured to identify a set of pacing parameters for different cardiac loads, and store them in a memory 274. The therapy control module 282 may be programmed to deliver a pacing therapy to the patient's heart using the identified set of pacing parameters (Block 612). These steps may be repeated on a continuing basis to increase and/or decrease the cardiac work of the heart as needed (Block 616).

Various pacing parameters may be used to increase or decrease the cardiac work of the heart. Exemplary pacing parameters that may be adjusted and/or optimized to change the hemodynamic efficiency and/or cardiac output of the heart include, but are not limited to: atrial-ventricular delay (A-V delay), interventricular delay (V-V delay, interatrial delay (A-A delay), intersite pacing delays, tracking or non-tracking operation, pacing sites, pacing vectors, pacing rate limits, pacing pulse amplitude, pacing pulse width, and/or the like. In one example, and as shown in FIG. 3, the therapy control module 282 may be programmed to pace the heart using a first A-V delay (e.g. 200 msec) during a first period of time to increase the cardiac work of the heart, and to pace the heart using a second A-V delay (e.g. 100 or 250 msec) during a second period of time to decrease the cardiac work of the heart relative to the cardiac work achieved during the first period of time. In another example, the therapy control module 282 may be programmed to pace the heart using a first V-V delay during a first period of time to increase the cardiac work of the heart, and to pace the heart using a second V-V delay during a second period of time to decrease the cardiac work relative to the cardiac work achieved during the first period of time. In yet another example, the therapy control module 282 may be programmed to pace the heart using a first pacing voltage amplitude during a first period of time to increase the cardiac work of the heart, and to pace the heart using a second voltage amplitude during a second period of time to decrease the cardiac work relative to the cardiac work achieved during the first period of time. In still yet another example, the therapy control module 282 may be programmed to pace the heart using a first pacing pulse width during a first period of time to increase the cardiac work of the heart, and to pace the heart using a second pacing pulse width during a second period of time to decrease the cardiac work relative to the cardiac work achieved during the first period of time. These are just some examples.

In some cases, the therapy control module 282 may be programmed to pace the heart using a set of pacing parameters that may increase or decrease the contractility of the heart under selected conditions. The maximum Left Ventricle (LV) dP/dT, which may be estimated via the amplitude of the first heart sound S1 (see FIG. 2), may be related to the Left Ventricle (LV) contractility of the heart. The therapy control module 282 may be programmed to pace the heart using a first set of pacing parameters to increase the maximum LV dP/dT to increase the cardiac output of the heart during a first period of time, and to pace the heart using a second set of pacing parameters to relatively decrease the maximum LV dP/dT to intentionally provide a relatively lower cardiac output of the heart during a second period of time relative to the LV dP/dT achieved during the first period of time. The decrease in maximum LV dP/dT experienced during the second period of time using the second set of pacing parameters may be relative to the maximum LV dP/dT achieved during the first period of time using the first set of pacing parameters. In some cases, the left ventricular contractility or maximum LV dP/dT achieved during the second period of time may be less than about 90 percent, less than about 80 percent, less than about 70 percent, less than about 60 percent or more of the left ventricular contractility or maximum LV dP/dT achieved during the first period of time. In some cases, the left ventricular contractility or maximum LV dP/dT achieved during the second period of time may range from about 50 percent to about 90 percent less than the left ventricular contractility or maximum LV dP/dT during the first period of time.

In some cases, the therapy control module 282 may be programmed to pace the heart using a set of pacing parameters using two or more pacing vectors. As indicated above, each combination of pacing electrodes used can be considered a different pacing "vector". In some cases, the pacing vectors may be selected and used during pacing in addition to, or in place of, the pacing parameters identified above to increase or decrease the cardiac output of the heart under selected conditions. For example, the therapy control module 282 may be programmed to select a first pacing vector under a first condition and a second pacing vector under a second condition. In some cases, the first condition corresponds to a period of time in which the patient is more active or awake, and the second condition may correspond to a period of time in which the patient is less active or asleep. In some cases, the first condition may correspond to a wake period during a circadian rhythm of the patient, and the second condition may correspond to a sleep period during a circadian rhythm of the patient. In another non-limiting example, the first condition may correspond to when the patient has a first posture (e.g. standing), and the second condition may correspond to a period of time when the patient has a second posture (e.g. sitting or lying down). In yet another example, the first condition may correspond to a period of time when the patient is at a first activity level (e.g. engaging in some level of physical activity), and the second condition may correspond to a period of time when the patient is at a second activity level that is different from the first activity level (e.g. resting, sitting, reading, etc.). These are just some examples.

Figure 7:
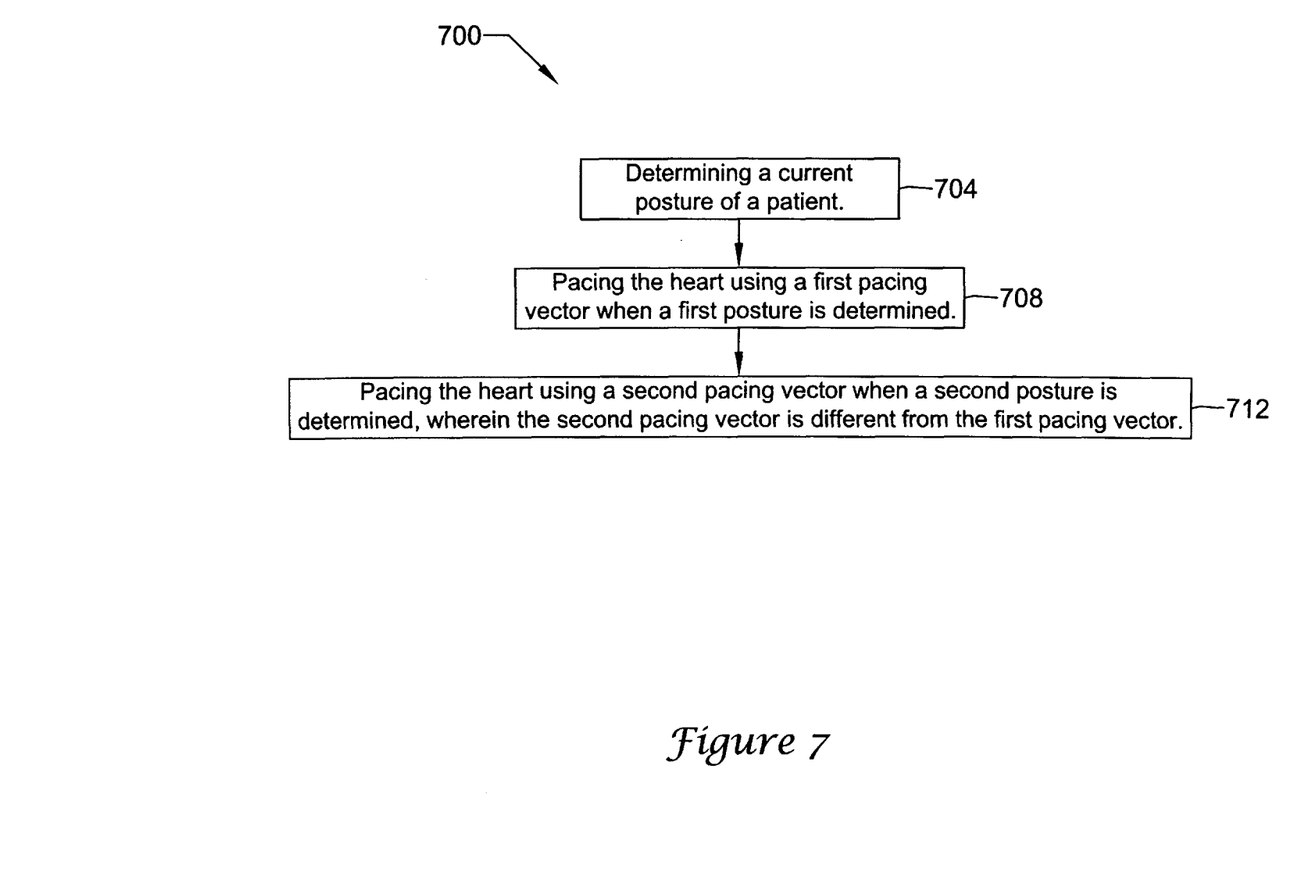
FIG. 7 is a flow chart of another illustrative method of pacing a patient's heart using an IMD.

FIG. 7 is a flow chart outlining an illustrative method 700 of pacing the heart when the IMD 101 has two or more pacing electrodes that can pace the heart using two or more pacing vectors. According to the illustrative method 700, the programmable controller 224 may determine a current posture of the patient (Block 704). In response, the therapy control module 282 may select a first pacing vector for the current posture of the patient and use the first pacing vector to pace the heart (Block 708). In response to a change in posture of the patient, the programmable controller 224 may determine a second posture of the patient. The therapy control module 282 may then select a second pacing vector in response to the change in posture of the patient and use the second pacing vector to pace the heart (Block 712). The different pacing vectors may be used to pace the heart in addition to, or in place of, the other pacing parameters (e.g. A-V delay, V-V delay, pulse width, voltage, etc.) identified above to increase or decrease the cardiac output of the heart under selected conditions.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method for pacing a heart of a patient via an implantable pacing device, the method comprising:
   during a first period of time, delivering electrical pacing to at least one of an atrium or a ventricle of the heart to increase the left ventricular contractility to produce an increased cardiac output; and
   determining a second period of time when an activity level of the patient is less than an activity level of the patient during the first period of time, delivering the electrical pacing stimulation in response to detecting the second period of time to decrease the left ventricular contractility to a specified fraction of the left ventricular contractility achieved during the first period of time to produce a reduced cardiac output.

2. The method of claim 1, wherein the first period of time corresponds to a wake period during a circadian rhythm of the patient, and the second period of time corresponds to a sleep period during the circadian rhythm of the patient.

3. The method of claim 1, wherein the first period of time corresponds to a period when the patient has a first posture, and the second period of time corresponds to a period when the patient has a second posture.

4. The method of claim 1, wherein the left ventricular contractility achieved during the second period of time ranges from about 60 percent to about 90 percent of the left ventricular contractility achieved during the first period of time.

5. The method of claim 1, wherein the left ventricular contractility is measured by LV dP/dT Max.

6. The method of claim 1, wherein during the first period of time, the heart is paced using a first A-V delay, and during a second period of time, the heart is paced using a second A-V delay that is different from the first A-V delay.

7. The method of claim 1, wherein during the first period of time, the heart is paced using a first V-V delay, and during a second period of time, the heart is paced using a second V-V delay that is different from the first V-V delay.

8. The method of claim 1, wherein during the first period of time, the heart is paced using a first pacing voltage, and during a second period of time, the heart is paced using a second pacing voltage that is different from the first pacing voltage.

9. The method of claim 1, wherein during the first period of time, the heart is paced using a first pacing pulse width, and during a second period of time, the heart is paced using a second pacing pulse width that is different from the first pacing pulse width.

10. The method of claim 1, wherein during the first period of time, the heart is paced using a first pacing vector, and during a second period of time, the heart is paced using a second pacing vector that is different from the first pacing vector.

11. The method of claim 1, wherein the left ventricular contractility is determined using the amplitude of a first heart sound S1.

12. The method of claim 1, further comprising:
selecting a first set of pacing parameters to increase the left ventricular contractility to produce an increased cardiac output during the first period of time;
selecting a second set of pacing parameters to decrease the left ventricular contractility relative to the left ventricular contractility achieved during the first period of time to produce a reduced cardiac output; and
wherein, if one or more sensors indicate that the second set of pacing parameters may adversely impact a function of the patient's heart, reverting back to the first set of pacing parameters.

13. A method for pacing a heart of a patient via an implantable pacing device, the method comprising:
during a first period of time, delivering electrical stimulation to at least one of an atrium or ventricle of the heart to increase the cardiac work of the heart wherein cardiac work is representative of energy efficiency of the heart; and
determining a second period of time when an activity of the patient is less than an activity level of the patient during the first period of time;
delivering the electrical pacing stimulation when an activity level of the patient is less than an activity level of the patient during the first period of time to decrease the cardiac work of the heart to a specified fraction of the cardiac work achieved during the first period of time.

14. The method of claim 13, wherein the cardiac work achieved during the second period ranges from about 60 to 90 percent of the cardiac work achieved during the first period of time.

15. The method of claim 13, wherein the first period of time corresponds to a wake period during a circadian rhythm of the patient and the second period of time corresponds to a sleep period during the circadian rhythm of the patient.

16. The method claim 13, wherein cardiac work is estimated based on an area within a pressure-volume loop, where heart sounds are used to estimate pressure changes, and impedance can be used to estimate volume changes.

* * * * *